US011135358B2

(12) United States Patent
Bode

(10) Patent No.: US 11,135,358 B2
(45) Date of Patent: Oct. 5, 2021

(54) DRUG DELIVERY DEVICE

(71) Applicant: SANOFI-AVENTIS DEUTSCHLAND GMBH, Frankfurt am Main (DE)

(72) Inventor: Andreas Bode, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 650 days.

(21) Appl. No.: 15/760,710

(22) PCT Filed: Sep. 5, 2016

(86) PCT No.: PCT/EP2016/070884
§ 371 (c)(1),
(2) Date: Mar. 16, 2018

(87) PCT Pub. No.: WO2017/045960
PCT Pub. Date: Mar. 23, 2017

(65) Prior Publication Data
US 2018/0250466 A1    Sep. 6, 2018

(30) Foreign Application Priority Data

Sep. 18, 2015 (EP) .................................... 15185787

(51) Int. Cl.
*A61M 5/20* (2006.01)
*A61M 5/145* (2006.01)
(Continued)

(52) U.S. Cl.
CPC ...... *A61M 5/14566* (2013.01); *A61M 5/3146* (2013.01); *A61M 5/1452* (2013.01); *A61M 5/31513* (2013.01); *A61M 2005/2411* (2013.01)

(58) Field of Classification Search
CPC ........ A61M 2005/2411; A61M 5/1452; A61M 5/14566; A61M 5/3146; A61M 5/31513
See application file for complete search history.

(56) References Cited

U.S. PATENT DOCUMENTS

2004/0176729 A1* 9/2004 Langley ............ A61M 5/31553
604/207
2008/0167618 A1* 7/2008 Sharifi .............. A61M 5/14566
604/151
(Continued)

FOREIGN PATENT DOCUMENTS

EP         1944048      7/2008
WO    WO 2013/007769    1/2013
(Continued)

OTHER PUBLICATIONS

International Preliminary Report on Patentability in International Application No. PCT/EP2016/070884, dated Mar. 20, 2018, 8 pages.
(Continued)

*Primary Examiner* — Rebecca E Eisenberg
(74) *Attorney, Agent, or Firm* — Fish & Richardson P.C.

(57) ABSTRACT

The present disclosure relates to a drug delivery device for dispensing of a liquid medicament, the device comprising:
a housing to accommodate a cartridge filled with the medicament and having a piston slidably displaced inside the cartridge along an axial direction and sealing a proximal end of the cartridge,
a drive mechanism having a piston rod extending along the axial direction and being at least displaceable from a proximal end position in distal direction to displace the piston in distal direction,
at least one distal support facing in proximal direction to axially abut a distally facing support face of the cartridge, (Continued)

wherein an axial distance between the distal support and a distal end of the piston rod when in the proximal end position is smaller than an effective length of the cartridge, which effective length is determined as the axial distance between a proximal face of the piston and the distally facing support face.

17 Claims, 3 Drawing Sheets

(51) Int. Cl.
  *A61M 5/31* (2006.01)
  *A61M 5/24* (2006.01)
  *A61M 5/315* (2006.01)

(56) References Cited

U.S. PATENT DOCUMENTS

2016/0206853 A1* 7/2016 Bolduc ............ A61M 25/0133
2017/0157340 A1* 6/2017 Moeller ................. A61M 5/24

FOREIGN PATENT DOCUMENTS

| WO | WO 2014/139918 | 9/2014 |
| WO | WO 2015/007814 | 1/2015 |
| WO | WO 2015/007818 | 1/2015 |

OTHER PUBLICATIONS

International Search Report and Written Opinion in International Application No. PCT/EP2016/070884, dated Dec. 8, 2016, pages.

* cited by examiner

DRUG DELIVERY DEVICE

CROSS REFERENCE TO RELATED APPLICATIONS

The present application is the national stage entry of International Patent Application No. PCT/EP2016/070884, filed on Sep. 5, 2016, and claims priority to Application No. EP 15185787.7, filed on Sep. 18, 2015, the disclosures of which are expressly incorporated herein in entirety by reference thereto.

TECHNICAL FIELD

The present disclosure relates to the field of drug delivery devices and in particular to the field of injection devices for delivery of a liquid medicament by way of injection.

BACKGROUND

Drug delivery devices for setting and dispensing a single or multiple doses of a liquid medicament are as such well-known in the art. Generally, such devices have substantially a similar purpose as that of an ordinary syringe.

Drug delivery devices and in particular injection devices have to meet a number of user-specific requirements. For instance, with patient's suffering chronic diseases, such like diabetes, the patient may be physically infirm and may also have impaired vision. Suitable drug delivery devices especially intended for home medication therefore need to be robust in construction and should be easy to use. Furthermore, manipulation and general handling of the device and its components should be intelligible and easy understandable. Moreover, a dose setting as well as a dose dispensing procedure should be easy to operate and unambiguous.

The medicament to be dispensed by the drug delivery device is provided and contained in a multi-dose cartridge. Such cartridges typically comprise a vitreous barrel sealed in distal direction by means of a pierceable seal and being further sealed in proximal direction by a piston, typically made of an elastomeric material. With reusable drug delivery devices an empty cartridge is replaceable by a new one. In contrast to that, drug delivery devices of disposable type are to be entirely discarded when the cartridge is empty.

Automated medicament delivery devices, such like auto-injectors or infusion pumps provide a rather easy and convenient approach to inject a predefined dose of a liquid medicament into biological tissue. Extraction and withdrawal of the medicament is often realized by means of a piston rod of a drive mechanism operable to exert a driving pressure onto a piston of the cartridge, thereby displacing the piston in distal direction to expel a well-defined amount of the liquid medicament from the interior of the cartridge.

Delivery devices equipped with an electric drive and hence with an electrically-operated piston rod are typically configured as a reusable device allowing replacement of an empty cartridge by a new one. Upon deploying the device and prior to extract an initial dose from a new cartridge the cartridge has to be mounted inside the drug delivery device. In either case the time interval between a manufacturing and filling of a cartridge and an initial use of the cartridge by means of the drug delivery device or injection device may be comparatively long. At least some days, weeks, months or even years may have passed from the manufacturing of the cartridge and its initial use in or with a suitable drug delivery device.

Depending on a storage time or the shelf life of a cartridge a breakaway or break-loose force to be applied onto the piston may be substantially high for driving the piston in distal direction relative to the barrel of the cartridge. Therefore, an initial force to be applied to the piston for displacing the same in distal direction may be quite large. This generally requires implementation of rather large and powerful electrical drives.

The implementation of rather large, powerful and also heavy weight drives in drug delivery devices is of particular disadvantage when the drug delivery device is intended for a mobile use, where weight, space and storage of electric energy are of particular relevance.

Some aspects of the disclosure can be implemented to provide an improved drug delivery device for dispensing of a liquid medicament, typically by way of injection. The drug delivery device or the injection device provides an effective and simple means to overcome an initial breakaway force or break-loose force necessary to displace a piston inside a barrel of a cartridge after the piston has been subject to a short-term or long-term storage prior to its use in the drug delivery device. The improvements to be made to the drug delivery device are rather simple and cost-efficient and are easy to implement into existing designs of drug delivery devices. Optionally, the improvements to be made to the drug delivery device are suitable for retrofitting of existing drug delivery devices.

SUMMARY

In one aspect, the disclosure relates to a drug delivery device for dispensing of a liquid medicament. The disclosure particularly relates to injection devices that provide dispensing of a single or multiple well-defined doses of a liquid medicament and further provides injection of the liquid medicament into biological tissue of a patient. The drug delivery device comprises a housing to accommodate a cartridge filled with the liquid medicament. The cartridge typically has a piston that is slidably displaced inside the cartridge along an axial direction. Typically, the cartridge comprises a tubular-shaped barrel extending along an axial or longitudinal direction. The piston seals a proximal end, hence a longitudinal end of the cartridge. An opposite end, hence a distal end of the cartridge typically comprises or forms an outlet through which the liquid medicament can be extracted or expelled from the interior of the cartridge.

The drug delivery device further comprises a drive mechanism having at least a piston rod that extends along the axial or longitudinal direction of the cartridge. The piston rod is at least displaceable from a proximal end position in distal direction to displace the piston in distal direction accordingly. Furthermore, the drug delivery device or its housing also comprises at least one distal support that faces in proximal direction to axially abut a distally facing support face of the cartridge. The distal support acts as a distal stop, a distal abutment or as a distally positioned fastening structure for the cartridge inside the housing of the drug delivery device. The distal support defines an axial position of the cartridge, namely when the distally facing support face of the cartridge is in axial abutment with the proximally facing distal support of the drug delivery device. In other words, the at least one distal support of the drug delivery device defines an axial position of the cartridge inside the housing of the device.

Furthermore, an axial distance between the distal support and a distal end of the piston rod is smaller than an effective length of the cartridge if the piston rod is in its proximal end position. The distal support is typically located distally from the distal end of the piston rod. Hence, when the piston rod is in its proximal end position the axial distance between the distal support and the distal end of the piston rod is maximal. But this maximum axial distance is still smaller than the effective length of the cartridge. In the present context, the effective length of the cartridge is determined as the axial distance between a proximal end face of the piston and the distally facing support face of the cartridge. Typically, the proximal face of the piston is in direct axial abutment with the distal end of the piston rod.

Since an axial distance between the distal support and the distal end of the piston rod is smaller than the effective length of the cartridge the interior of the cartridge is either pressurized and/or the piston thereof is axially squeezed as the cartridge is arranged in a final assembly configuration inside the housing of the drug delivery device. By making the axial distance between the distal support and the piston rod's distal end in the proximal end position of the piston rod smaller than the effective length of the cartridge, it is somehow guaranteed, that a respective distally directed pressure or thrust is applied to the piston of the cartridge as the cartridge reaches a final assembly or a deployed position inside the housing of the drug delivery device.

In this way, the piston and/or the interior of the cartridge is at least somewhat pre-tensed in distal direction. The magnitude of this pressure or axial tension may depend on various parameters, such like manufacturing tolerances of the barrel of the cartridge, elasticity of the piston and the difference between the above mentioned axial distance between distal support and distal end and the effective length of the cartridge. In any case and with regard to the manufacturing or assembly tolerances the difference between the axial distance of distal support and distal end of the piston rod and the effective length of the cartridge is always larger than any conceivable manufacturing or assembly tolerance of the cartridge and the housing. In this way the piston is always subject to a distally directed pressure upon a final assembly inside the housing of the drug delivery device.

Investigations have revealed that a first or an initial displacement of the piston inside the cartridge after long-term or even short-term storage of the cartridge requires an initial force level that is much larger than a force level normally to be applied to a non-moving piston at the beginning of frequent dispensing procedures. In some application scenarios the piston might be subject to a single continuous displacement for emptying the cartridge in one go. In such a scenario the cartridge is only subject to dynamic friction after it has set in motion initially. In other typical scenarios of use the medicament is dispensed or injected in accordance with a predefined administering schedule according to which several doses of the medicament are dispensed and extracted from the cartridge at consecutive times, wherein the time intervals between consecutive dispensing procedures are rather small compared to the storage time between manufacturing of the cartridge and its initial use with the drug delivery device.

Hence, it is only at the very beginning and with an initial displacement of the piston inside the cartridge that a rather large force has to be applied to the piston in order to overcome the comparatively large break-loose or breakaway force of the piston relative to the barrel of the cartridge. A rather powerful drive mechanism for extracting the medicament from the cartridge would be only needed at the very beginning of the extraction of the medicament from the cartridge.

By means of the above mentioned pre-tension of the cartridge upon final assembly inside the device an initial displacement of the piston relative to the barrel of the cartridge and a very simple but rather effective means is provided to overcome the comparatively large breakaway or break-loose force of the piston. Consequently, the drug delivery device can be equipped with a less powerful drive that requires less assembly space, which comes along with a reduced weight and which is operable with reduced electrical power compared to conventional drive-operated drug delivery devices.

Accordingly, the axial distance between the distal support and the distal end of the cartridge in comparison to a given effective length of the cartridge provides a well-defined force effect or pressure onto the piston of the cartridge in an initial configuration. This is of particular use to reduce the dimensions, the weight, the costs as well as the overall energy consumption of the drug delivery device.

According to a further embodiment the distal support is located inside the housing and is further configured to axially abut with a distally facing radially extending shoulder portion of the cartridge. Typically, the cartridge comprises a tubular-shaped barrel extending into a radially narrowed neck portion towards its distal end. In distal direction the neck portion extends into a slightly radially widened head that serves as a dispensing end of the cartridge. In a transition area between the tubular-shaped barrel and the radially narrowed neck portion the shoulder portion of the cartridge is located.

The shoulder portion may comprise a rather slanted or beveled contour with regard to the axial direction. It may almost extend in a plane substantially perpendicular to the axial direction of the cartridge. The distal support is typically located at such a position inside the housing, that the axial distance between the distal support and the distal end of the piston rod when in the proximal end position is smaller than the effective length of the cartridge. Typically, the proximal face of the piston is located at an axial distance from the proximal end of the barrel of the cartridge. The proximal face of the piston might be located distally from the proximal end of the cartridge. The shoulder portion of the cartridge effectively acts and serves as the distally facing support face to axially abut with the distal support of the drug delivery device.

For an assembly of the cartridge inside the housing of the drug delivery device the cartridge may be inserted into the housing in a rather slanted or pivoted configuration compared to the axial direction of the piston rod. Here, the proximal face of the piston may be brought in direct axial contact with the distal end of the piston rod. Thereafter and by exerting at least a slight proximally directed pressure onto the barrel of the cartridge the cartridge can be aligned along the axial or longitudinal direction of the piston rod, thereby axially squeezing the cartridge between the distal support in abutment with the cartridge's shoulder portion and the distal end of the piston rod.

Such an embodiment is of particular use, when the housing comprises a lid or any other detachable housing component that provides access to the sidewall of the cartridge. Here, the cartridge has to be replaced and inserted into the housing by way of a movement in radial direction with respect to the axial elongation of the piston rod.

According to a further embodiment the drug delivery device further comprises a support member. The support member is either immovable affixed to the housing, thereby forming the distal support. In an alternative embodiment the support member is axially displaceable between a release position and a pre-tensed or deployed position inside the housing. The support member may comprise an axially displaceable latch that may be secured and fixed in the pre-tensed position thereby forming the distal support. In the release position the support member may be axially displaced compared to the pre-tensed or deployed position. When in the release position the axial distance between the support member and the distal end of the piston rod when in the proximal end position may be equal to or larger than the effective length of the cartridge.

In the release position a rather easy and intuitive replacement or insertion of the cartridge into the housing is enabled. It is then by way of the axial displacement of the support member into its proximally directed pre-tensed position that the intended pre-tension is established on the piston of the cartridge. Here, the support member may axially engage with the shoulder portion of the cartridge or with the distal end of the cartridge. By way of displacing the support member from the release position into the pre-tensed position the cartridge will be displaced accordingly in proximal direction until the distal end of the piston rod axially engages and axially abuts the proximal face of the piston and further until the piston is axially squeezed to a predefined degree or until the interior of the cartridge is pressurized to a predefined degree due to a slight distally directed movement of the piston relative to the barrel of the cartridge.

In another embodiment the housing comprises a lid moveable between a release position and a locking position to selectively close an access opening of the housing through which the cartridge is insertable into the interior of the housing. The lid may either be pivotable or translationally displaceable relative to the housing. The lid may even be detachable from the housing. In either case the lid and the housing comprise mutually corresponding fastening means, by way of which the lid is releasably or detachably connected to the housing in order to substantially close the access opening. The lid at least closes the housing to such a degree, that the cartridge is immovably fastened inside the housing. Closing of the lid and transferring the lid into its locking position keeps the cartridge inside the housing and prevents an uncontrolled removal of the cartridge from the housing. By opening the lid the cartridge may be replaced by a new one. By closing the lid the cartridge is securely fixable inside the housing.

With a pivotable lid even a leverage or leverage effect can be exploited. A contact point of the support face of the cartridge and the inside face of the lid may be located at a rather small radial distance to the pivot access compared to a portion of the lid that is subject to actuation through a user. In this way, the force effect exerted by a user and e.g. acting on a free end of the lid located opposite to the pivot axis or hinge of the lid may be subject to a leverage effect. Hence, the force acting on the cartridge in proximal direction as the lid is closed may be increased due to the leverage effect inherently provided by the pivotable lid.

According to a further embodiment an inside face of the lid forms the distal support when the lid is in the locking position. Hence, when the lid is in its locking or closed position its inside face may be in direct axial engagement or axial abutment with the distally facing support face of the cartridge.

Hence, the axial distance between the inside face of the lid when the lid is in the locking position and the distal end of the piston rod when the piston rod is in the proximal end position is smaller than the effective length of the cartridge. With this embodiment it is particularly conceivable that the lid acts as an axial displacement means, e.g. as a pusher for the cartridge. With an opened lid, the cartridge may be inserted into the housing of the drug delivery device. It may be then only and due to the closing of the lid and due to the transferring of the lid into its locking position that the cartridge experiences a proximally directed displacement until its piston is in direct axial abutment with the piston rod and until the piston experiences a well-defined pressure in distal direction. In its locking position the lid is interlocked and fastened to the housing.

According to a further embodiment the lid is pivotably attached to the housing. When in the locking position the lid may flush with an outer face of the housing. The lid may be positioned in a sidewall, front wall or back wall of the housing that faces towards the distal end of the cartridge when the cartridge is assembled inside the housing. It is particularly conceivable, that the lid, in particular its inside face gets in axial abutment with the distally facing support face of the cartridge prior to reach the locking position. Hence, during a pivoting or closing motion of the lid the inside face thereof typically gets in direct abutment or mechanical contact with the distally facing support face of the cartridge even before the lid reaches the locking position.

When in direct mutual mechanical contact a further pivoting or closing motion of the lid then leads to a proximally directed displacement of the cartridge inside the housing until the cartridge reaches its predefined position inside the housing. So when the locking position is reached, the inside face of the lid forming the distal support has an axial distance to the distal end of the piston rod that is smaller than the effective length of the cartridge. In this way, the cartridge is pre-tensed or biased, which means that either its interior is pressurized or that its piston is subject to a well-defined axial squeezing.

According to another embodiment the lid comprises a through opening to receive a connector that is configured to engage with a distal end of the cartridge in a fluid transferring way. The size of the through opening is typically much smaller than the distally facing support face of the cartridge. In some embodiments the distally facing support face of the cartridge may be formed by the distal-most end cap of the cartridge providing or acting as a pierceable seal. The through opening of the lid is typically sufficiently large to provide access to the pierceable section of the head of the cartridge so as to insert some type of connector, e.g. in form of a tipped cannula or the like extending through the seal and into the interior of the cartridge.

In other embodiments it is even conceivable that the shoulder portion of the cartridge has to be regarded as the distally facing support face. Then the through opening in the lid may be as large as to receive the head as well as a part of the neck portion of the cartridge. In such an embodiment the distal head of the cartridge may even protrude from the closed lid. The connector to be connected with the distal end of the cartridge in a fluid transferring way may be configured in many different ways. The connector may simply comprise a tipped cannula or a spike to provide fluid transferring access to the interior of the cartridge, simply by penetrating the pierceable seal thereof. In other embodiments it is conceivable that the cartridge comprises a standardized connector, such like a male or female Luer-type connector. Then the connector may comprise a correspondingly shaped connecting structure, such like a female or male Luer-type connector. By having a through opening in the lid a fluid transferring access to the interior of the cartridge can be provided even when the cartridge is partially or completely located inside the interior of the housing of the drug delivery device.

According to another embodiment the lid is particularly configured to displace the cartridge in proximal direction against the piston rod when pivoted from the release position into the locking position. In a similar but different embodiment with a slidably displaceable lid it is conceivable that the lid comprises a beveled edge that equally serves to induce a proximally directed displacement of the cartridge towards the piston rod as the lid is transferred into its locking position. In either case the lid fulfills a double function. On the one hand it effectively closes the housing of the drug delivery device and in particular a compartment in which the cartridge is located. On the other hand the closing motion of the lid is transferred into a proximally directed displacement of the cartridge, thereby providing the required pre-tension onto the piston of the cartridge.

According to another embodiment the cartridge is actually assembled and arranged inside the housing of the drug delivery device. The drug delivery device may be configured as a disposable or as a reusable device with a cartridge preassembled therein. Since the cartridge is subject to a mechanical load as it reaches its final assembly configuration or as the lid is transferred into its locking position it is of particular benefit, when the cartridge is manually inserted or assembled inside the housing only shortly before an initial dose of the medicament is to be dispensed or injected. It is further conceivable that the cartridge is readily mounte dor pre-assembled in an undeployed position or configuration inside the housing of the device. It may be then just by displacing the cartridge into the final assembly position or deployed position that the cartridge experiences the above described pre-stress or pressure.

According to a further embodiment the distal end of the piston rod is in axial abutment with the proximal face of the piston of the cartridge when the cartridge is in axial abutment with the distal support. This is a logical consequence from the requirement that the axial distance between the distal support and a distal end of the piston rod when in the proximal end position is larger than the effective lengths of the cartridge. Typically the piston rod exerts a well-defined pressure onto the proximal face of the piston. Consequently, the piston may be subject to a slight but distinct axial displacement relative to the sidewall of the barrel of the cartridge. In such case the pressure exerted to the proximal face of the piston is somewhat larger than the pressure required to overcome the break loose force of the piston with regard to the cartridge's sidewall.

Such a distally directed but distinct axial displacement of the piston relative to the sidewall of the cartridge typically leads to a well-defined pressure build up inside the interior of the cartridge. Such an initial pressure application may be beneficial for conducting an initial priming procedure, during which air contained in the cartridge or in a tubing in fluid connection with the cartridge has to be expelled. Imagine the cartridge being pressurized to a well-defined degree as correctly assembled inside the drug delivery device and subsequently connected some type of fluid transferring connector to the cartridge excess air or excess medicament can immediately and automatically escape. In this way, a separate step of priming could become substantially superfluous.

Accordingly and with a further embodiment at least one of the interior of the cartridge and the piston is pressurized or axially squeezed when the cartridge is axially supported by the distal support while the piston rod is in the proximal end position. In this way and as already described above, the cartridge can be pre-tensed and an initial priming procedure can become superfluous even without the necessity of displacing the piston rod from its proximal end position towards a distal position. The mechanical implementation of the drive mechanism, in particular in view of a dose counter can be thus simplified if a priming procedure does not have to be conducted and manually initialized by the end user or patient.

According to another embodiment the drive mechanism comprises an electric drive and a gear. The piston rod is operably engaged with the electric drive via said gear. The gear is typically implemented as a reduction gear. Hence, the piston rod rotates much slower than the electric drive with the effect, that the piston rod can be rotated with a respectable torque. The drive mechanism may further comprise an electronic control, typically having a memory and a processor. The control may be implemented on a printed circuit board. It may be coupled to various input and output means. The control may be electrically connected to some kind of display and some kind of buttons or regulators by way of which the overall operation of the drug delivery device and of its drive mechanism can be controlled by a user.

According to another embodiment the gear is of self-locking type. Typically, the interaction of the piston rod and the gear is of self locking type. Hence, a thrust or pressure acting on the piston rod in proximal direction does not lead to a rotation of the piston rod or of the gear operably coupled thereto. In this way application of a distally directed pressure onto the piston rod upon final assembly of the cartridge inside the drug delivery device has substantially effectless on the operation of the gear and the electric drive.

According to another aspect the disclosure also relates to a method of deploying a cartridge in a drug delivery device or to a method of assembling a cartridge in a drug delivery device in a final assembly configuration. The method comprises the steps of inserting a cartridge into a housing of a drug delivery device as described above. The cartridge is filled with a medicament and has a piston slidably displaced therein along an axial direction. The piston further seals a proximal end of the cartridge. In a further step either the interior of the cartridge is pressurized and/or the piston of the cartridge is axially squeezed by bringing a distally facing support face of the cartridge in axial abutment with a distal support of the drug delivery device, such that a proximal face of the cartridge, in particular of its piston gets or is in abutment with a distal end of the piston rod of the drug delivery device, while the piston rod is and remains in its proximal end position.

Pressurizing or axially squeezing of at least one of the interior of the cartridge and the piston may occur during or after insertion of the cartridge into the housing of the drug delivery device. It is particularly conceivable, that the cartridge is positioned in a pre-assembly configuration inside the housing of the drug delivery device in a rather uncompressed or non-biased way. It may then only by way of transferring a lid into a locking position that the cartridge experiences a proximally directed displacement relative to the housing and hence relative to the piston rod, thereby squeezing the piston and/or displacing the piston in distal direction relative to the barrel of the cartridge.

According to a further embodiment of said method the interior of the cartridge or the piston thereof is pressurized or axially squeezed by moving a lid of the housing into a locking position, thereby bringing an inside face of the lid in axial abutment with a distally facing support face of the cartridge prior to reach a locked position. Thereafter and during a further movement of the lid towards its locked position the cartridge is displaced in proximal direction under the action of the moving lid. Hence, the lid actually serves as a means to move the cartridge to its predefined position inside the drug delivery device.

In the present context the distal direction denotes a dispensing end of the drug delivery device. When the drug delivery device is implemented as an injection device the distal end of the drug delivery device faces towards an injection site of a patient. The proximal end or the proximal direction faces in the opposite longitudinal direction of the device. When implemented as an injection device, the proximal end of the drug delivery device is typically operable by a hand of a user so as to configure, to set and to conduct an injection procedure.

The term "drug" or "medicament", as used herein, means a pharmaceutical formulation containing at least one pharmaceutically active compound,
wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound,
wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis,
wherein in a further embodiment the pharmaceutically active compound comprises at least one peptide for the treatment and/or prophylaxis of diabetes mellitus or complications associated with diabetes mellitus such as diabetic retinopathy,
wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyldes(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser- Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4 (1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4 (1-39)-(Lys)6-NH2,
H-(Lys)6-des Pro36 [Trp(02)25, Asp28] Exendin-4(1-39)-Lys6-NH2,
H-des Asp28 Pro36, Pro37, Pro38 [Trp(O2)25] Exendin-4 (1-39)-NH2,
H-(Lys)6-des Pro36, Pro37, Pro38 [Trp(02)25, Asp28] Exendin-4(1-39)-NH2,
H-Asn-(Glu)5-des Pro36, Pro37, Pro38 [Trp(02)25, Asp28] Exendin-4(1-39)-NH2,
des Pro36, Pro37, Pro38 [Trp(02)25, Asp28] Exendin-4(1-39)-(Lys)6-NH2,
H-(Lys)6-des Pro36, Pro37, Pro38 [Trp(02)25, Asp28] Exendin-4(1-39)-(Lys)6-NH2,
H-Asn-(Glu)5-des Pro36, Pro37, Pro38 [Trp(02)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(02)25, Asp28] Exendin-4(1-39)-Lys6-NH2, H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

It will be further apparent to those skilled in the art that various modifications and variations can be made to the present invention without departing from the spirit and scope of the invention as it is defined by the claims. Further, it is to be noted, that any reference numerals used in the appended claims are not to be construed as limiting the scope of the invention.

BRIEF DESCRIPTION OF THE FIGURES

In the following, an embodiment of the display arrangement, the drive mechanism and the drug delivery device is described in detail by making reference to the drawings, in which.

DETAILED DESCRIPTION

Figure 1:
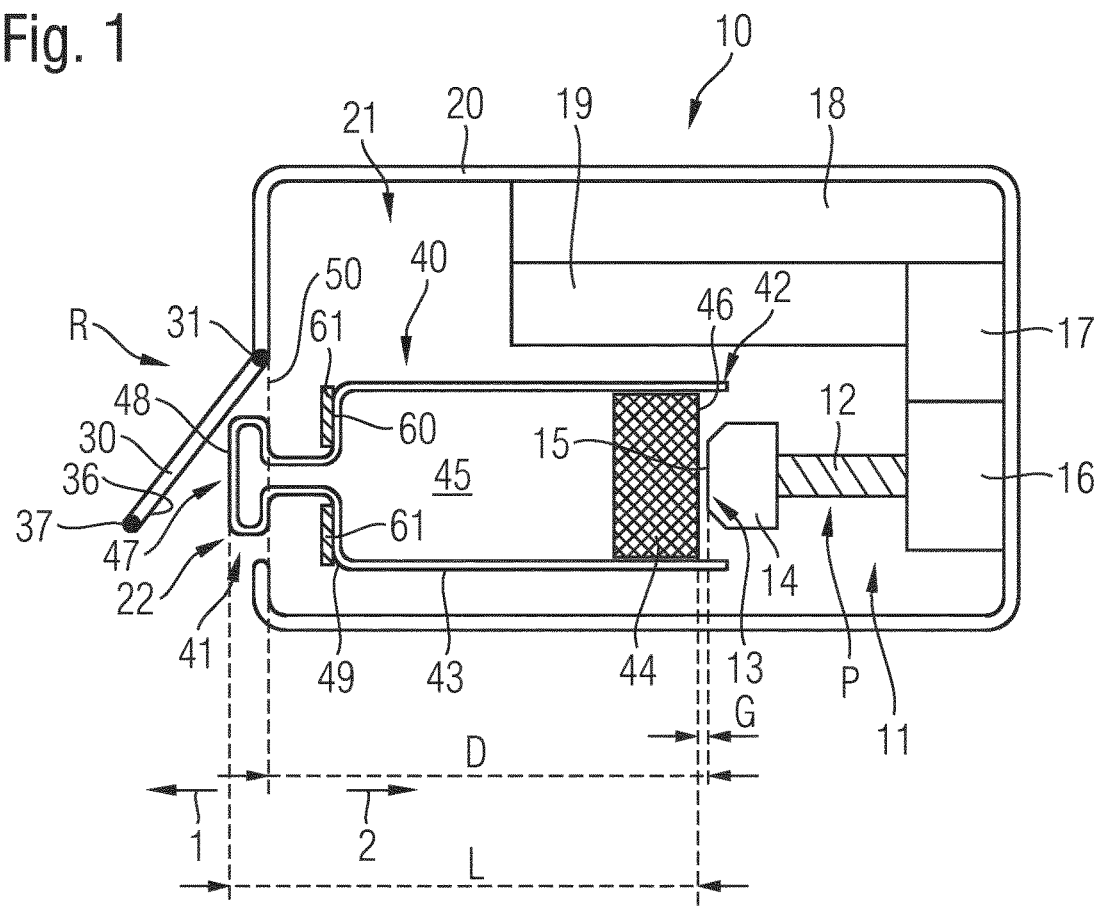
FIG. 1 schematically shows the drug delivery device with a cartridge assembled therein in a preassembly configuration prior reaching a final assembly position, FIG. 2 schematically shows the device according to FIG. 1 but with a closed lid and with the cartridge in the final assembly configuration.

In FIG. 1 the drug delivery device 10 is schematically illustrated. The drug delivery device 10 comprises a housing 20. The housing 20 is presently illustrated as a rectangular-shaped box. The housing 20 may also comprise any other type of geometric structure. For instance, the housing 20 may comprise a rather elongated shape and may resemble a pen. In such embodiments, presently not illustrated the drug delivery device 10 may form or comprise a pen-type injection device.

The presently illustrated embodiment of the drug delivery device 10 may reflect an infusion device, such like an infusion pump. The drug delivery device 10 comprises a drive mechanism 11. The drive mechanism 11 comprises an axially extending piston rod 12 that is displaceable in axial direction. As illustrated in FIG. 1, the axial direction is characterized by an axial distal direction 1 and by an opposite axial proximal direction 2. The distal end 13 of the piston rod 12 is provided with a pressure piece 14. Even though not particularly illustrated the piston rod 12 may be threadedly or rotatably engaged with a gear 16 which is powered by a drive 17.

Figure 2:
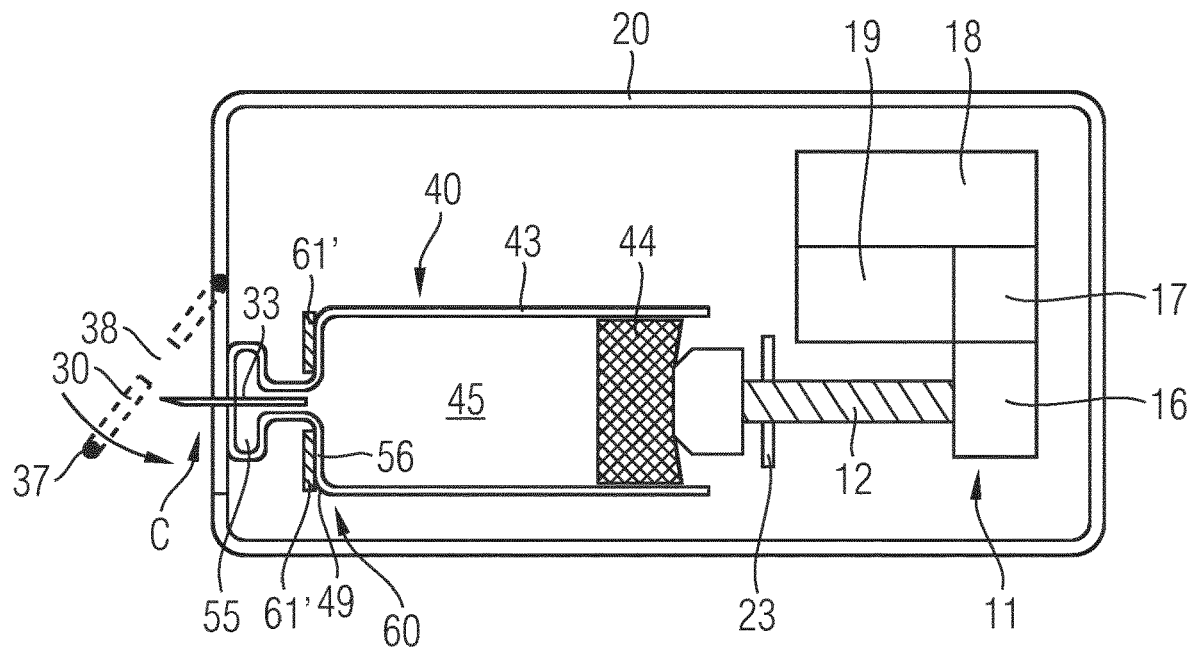

In the present embodiment the drive 17 is implemented as an electric drive that is controlled by a control 19 and which is powered by a battery 18. The control 19 may be implemented as a printed circuit board. It typically comprises at least one processor and a memory as well as various input/output means for processing data and for controlling the operation of the drive mechanism 11 and for communication with a user or patient. The piston rod 12 may comprise an outer thread that is threadedly engaged with a threaded support 23 connected to or integrally formed with the housing as shown in FIG. 2. The threaded support 23 comprises a threaded through opening through which the piston rod 12 extends in axial direction. In this way a rotation of the piston rod 12 relative to the housing 20 is accompanied by and leads to an axial displacement of the piston rod 12 relative to the housing 20. The distal end 13 of the piston rod 12 may be provided with a pressure piece 14. The pressure piece 14 may be freely rotatable at the distal end 13 of the piston rod 12. In this way and once the pressure piece 14 is in axial abutment with a proximal face 46 of a piston 44 of a cartridge 40 the rotating motion of the piston rod 12 does not transfer to the piston 44.

Apart from a threaded engagement of the piston rod 12 with the threaded support also other axial guiding structures between the piston rod 12 and the housing 20 are conceivable. It is for instance conceivable, that the piston rod 12 is only subject to a purely axial translational but non-rotative displacement during dispensing of a dose. This can be accomplished by a keyed or splined engagement with the support 23, which in this case may comprise a radially extending recess or protrusion engaging with a correspondingly-shaped protrusion or recess of the piston rod 12. In addition to an elongated and axially extending protrusion or groove the piston may also comprise a threaded section at least at a proximal end thereof, which threaded section is in rotational engagement with the gear 16.

In FIG. 1 an initial configuration of the drive mechanism 11, i.e. prior to dispensing and setting of an initial dose is schematically illustrated. Here, the piston rod 12 is in a proximal end position P. The interior 21 of the housing 20 is configured to accommodate a cartridge 40. The cartridge 40 comprises a distal end 41 and a proximal end 42. In a preassembly configuration as shown in FIG. 1 the cartridge 40 with its tubular-shaped barrel 43 is aligned substantially along the axial direction. The cartridge 40 is sealed in proximal direction 2 by means of a piston 44. The piston 44 extends over the entire inner cross-section of the tubular-shaped barrel 43. It is in sealing engagement with the inside facing sidewall portion of the barrel 43.

Between the piston 44 and the distal end 41 of the cartridge 40 there is provided a liquid medicament in the interior 45 of the cartridge 40. The distal end 41 of the cartridge 40 is provided with a proximal seal 47. Apparently, the seal 47 is located at the distal end of a radially widened head 55 of the barrel 40. The head 55 is integrally formed with the tubular-shaped barrel 43. Between the distal head 55 and the proximal portion of the barrel 43 there is located a radially narrowed neck portion 54. The tubular-shaped barrel 43 extends into the radially narrowed neck portion 54 via a radially narrowing shoulder portion 56 as illustrated in FIGS. 1 and 2.

In the preassembly configuration as shown in FIG. 1 the distal end face 48 of the cartridge 40 extends in distal direction 1 through an access opening 22 of the housing 20 through which access opening 22 the entire cartridge 40 is insertable into the interior 21 of the housing 20. As it is apparent from a comparison of FIGS. 1 and 2 the access opening 22 is closeable by means of a lid 30 that is pivot mounted to a sidewall of the housing 20. Here, an upper end of the lid 30 is connected to the housing 20 via a hinge 31. The hinge 31 thereby forms a pivot access extending perpendicular to the plane of the illustration of FIG. 1.

Moreover, in this preassembly configuration there may exist a small gap G between the distal face 15 of the piston rod 12 and a proximal face 46 of the piston 44 of the cartridge 40. By closing the lid 30 and by transferring the lid 30 from the release position R as shown in FIG. 1 into the locking position C as shown in FIG. 2 the inside face 36 of the lid gets in axial abutment with the distal end face 48 of the cartridge 40. Accordingly, the cartridge 40 experiences a proximally directed displacement relative to the housing 20 as the lid 30 is closed. The cartridge then assumes its deployed or final assembly configuration.

The lid 30 further has a through opening 38 through which a connector 33, presently implemented as a double-tipped needle may penetrate the distally located seal 47 of the cartridge 40. In the embodiment as shown in FIGS. 1 and 2 the inside face 36 of the lid 30 forms a distal support of the housing 20 when the lid 30 is in its locking position C as shown in FIG. 2. The distal support 50, hence the position of the inside face 36 of the lid 30 when in the locking position C is shown in FIG. 1 by means of a vertically extending dashed line. It is immediately apparent from FIG. 1, that closing of the lid 30, hence pivoting of the lid 30 in a counter clockwise direction inevitably leads to a proximally directed displacement of the cartridge 40 relative to the housing 20. Here, the distal face 48 of the cartridge 40 and the inside face 36 of the lid 30 get in direct mutual axial abutment before the lid reaches its locking position C. Moreover, it is apparent that the radial distance between a contact point of the lid 30 and the distally facing support face 48 of the cartridge 40 is smaller than the radial extension of the lid 30 with regard to the pivot axis of the hinge 31. Hence, by pushing the lid at its free end, in particular at or near its closure 37 or interlock that is located at a free end of the lid remote from the hinge 31 a leverage effect can be exploited thereby urging the cartridge 40 in proximal direction with a larger force effect compared to the force applied to the free end of the lid 30.

The dimensions of the housing 20, in particular the position of the inside face 36 of the lid 30 in comparison to the distal face 15 of the piston rod 12 when in the proximal end position P are selected such, that the axial distance D therebetween, hence the axial distance D between the distal support 50 and the distal end face 15 of the piston rod 12 is smaller than the effective length L of the cartridge 40. Here, the effective length L of the cartridge 40 is determined as the axial distance between the distally facing support face 48 of the cartridge and the proximal face 46 of the piston 44. Since the space provided in the housing 20 between the distal support 50 and the distal end 15 of the piston rod 12 is smaller than the effective length L the cartridge 40 is subject to an axial pre-stress, axial squeezing as the lid 30 is closed.

Figure 3:
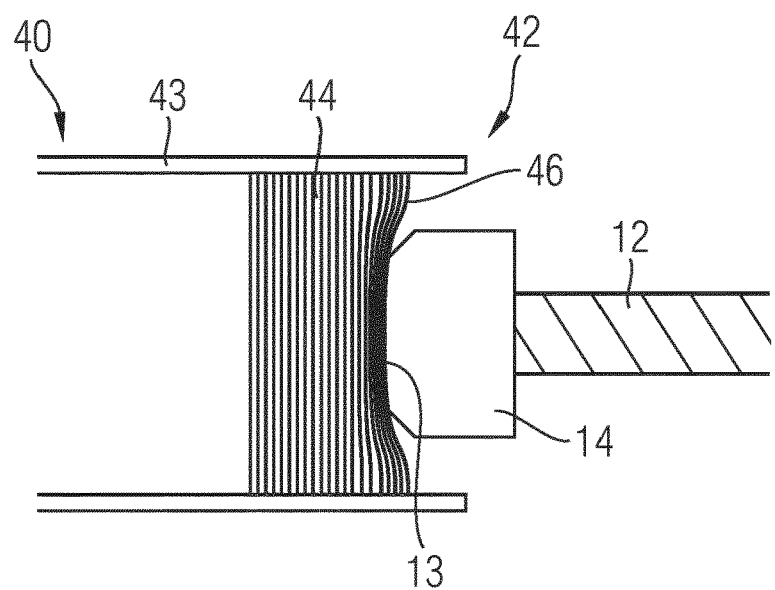
FIG. 3 is illustrative of an enlarged view of the interface of distal end of the piston rod and proximal end of the piston of the cartridge.

Consequently and during closing of the lid the cartridge 40 is initially displaced in proximal direction 2 until the gap G disappears so that the distal end 15 of the piston rod 12 gets in direct abutment with the proximal face 46 of the piston 44 of the cartridge 40. Reduction and elimination of the gap G typically occurs before the lid 30 reaches its locking position C. Consequently and during the rest of the pivoting motion of the lid 30 the cartridge 40 is further displaced in proximal direction 2 relative to the housing 20. Since the piston rod 12 cannot be further displaced in proximal direction, since it is already in an axially blocked or proximal end position P the piston 44 is subject to a distally directed force effect as it is shown in more detail in FIG. 3.

Figure 4:
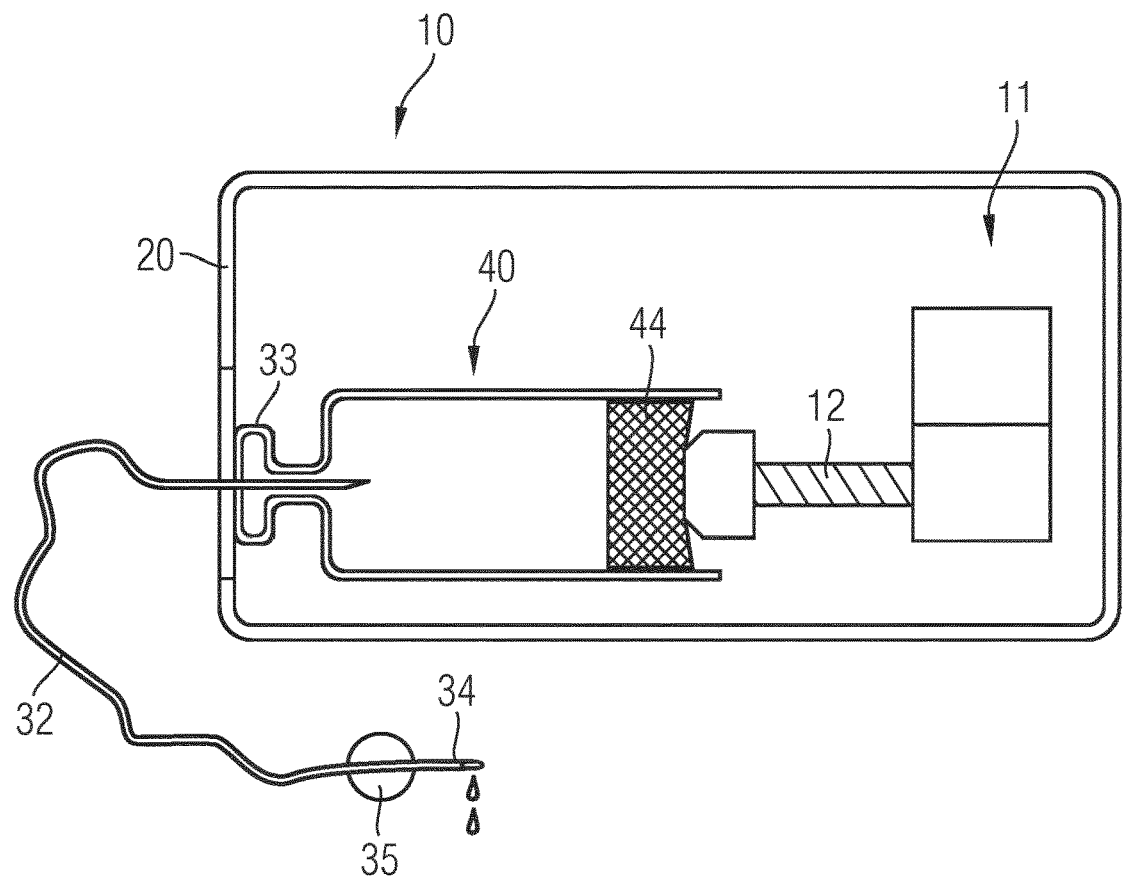
FIG. 4 is illustrative of a fluid transferring connection to the distal end of the cartridge when finally assembled inside the housing and FIG. 5 is a flowchart illustrating the method of deploying the cartridge inside the device.

In this way and without any displacement of the piston rod 12 the piston 44 can be pre-stressed. If the pressure applied to the piston 44 exceeds a break loose force the piston 44 even at least slightly displaces in distal direction 1 relative to the barrel 43, thereby pressurizing the liquid medicament contained inside the interior 45 of the cartridge 40. By establishing a fluid transferring connection to the interior 45 of the cartridge 40, e.g. by means of the connector 33 penetrating the distal seal 47 of the cartridge 40 a droplet generation may be observed at an opposite end of the connector 33. As illustrated in FIG. 4 the connector 33 may be in fluid communication with a tube 32. At an opposite or distal end of the tube 32 may be provided with a further connector 34, e.g. in form of a cannula that may be pierced into biological tissue with the help of a flap 35 attached to the tube 32 in direct vicinity of the connector 34. As soon as the connector 33 and the tube 32 get in fluid transferring connection with the interior 45 of the cartridge 40 the pressurized liquid medicament located therein may escape from the cartridge 40 until a pressure equilibrium with the environment is re-established. Such a pre-pressurized cartridge 40 may be beneficial to reduce or to eliminate an initial priming procedure which is originally intended to expel any air in the fluid transferring components of the drug delivery device 10.

In another embodiment which is also schematically illustrated in FIGS. 1 and 2 it is also conceivable that alternative to or in addition to the distal head 55 of the cartridge 40 a shoulder portion 56 of the cartridge 40 actually acts as the distally facing support face 49. Here, a support member 61 may either be immovably affixed to the housing 20 thereby forming the distal support 60. Upon insertion of the cartridge 40 into the interior 21 of the housing 20 the cartridge 40, in particular its tubular-shaped barrel 43 has to be squeezed between the distal support 60 and the distal end 15 of the piston rod 12. For this it may be particularly intended, that the piston 44 of the cartridge 40 is brought initially in abutment with the distal face 15 of the piston rod 12. Thereafter and by means of a kind of a pivoting motion supported by a slightly beveled shape of the shoulder portion 56 of the barrel 43 of the cartridge 40 the cartridge 40 may then experience a proximally directed displacement as it is pressed down into the compartment provided between the distal support 60 and the distal face 15 of the piston rod 12.

In a further embodiment as presently illustrated in FIGS. 1 and 2 the distal support 60 is realized by at least one or two support members 61 that are axially displaceable between a release position as shown in FIG. 1 and a pre-tensed position 61' as shown in FIG. 2. The release position is located distally from the pre-tensed position of the support member 61. In the release position the cartridge 40 may be easily inserted into the free space provided between the support member 61 and the distal end 15 of the piston rod 12. Here the axial distance between the support member 61 in the release position and the distal end 13 of the piston rod 12 is substantially equal to or larger than the effective length L of the cartridge 40. As shown in FIG. 1 the support member 61 may be in axial abutment with the shoulder portion 56 of the barrel 43 of the cartridge 40. A proximally facing section of the support member 61 is in axial abutment with a distally facing section of the shoulder portion 56, wherein the shoulder portion 56 forms the distally facing support face 49.

It is then due to a user controlled or user initiated proximally directed displacement of the support member 61 that the cartridge 40 is displaced in proximal direction 2 as shown in FIG. 2 thereby displacing the cartridge 40 to such an extent in proximal direction 2 that the lid 30 can be closed without any resistance that might be otherwise due to a collision with the distal end of the cartridge 40.

It is even conceivable, that such support members 61 acting on the shoulder portion of the cartridge and hence on the distally facing support face 49 of the cartridge 40 are connected or integrated into the lid 30. Hence, the lid may comprise inwardly extending protrusions that act substantially in the same way as the support members 61. In this way even existing devices could be easily retrofitted simply by modifying an existing lid 30.

Figure 5:
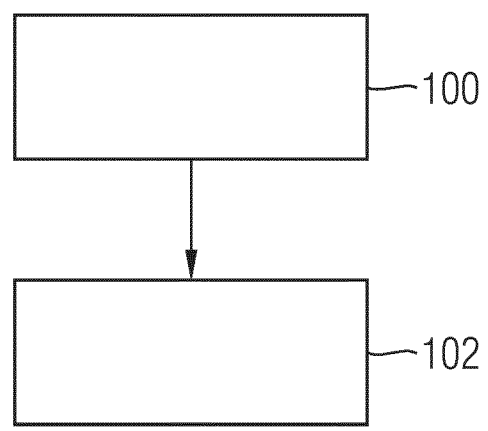

In FIG. 5 a flowchart for illustrating the steps of the method of deploying the cartridge or the pre-stressed cartridge 40 in the drug delivery device 10 is given. Here, in a first step 100 the cartridge 40 is inserted into the housing 20 of the drug delivery device 10. The cartridge may by positioned in a pre-assembly configuration is shown in FIG. 1, wherein the proximal face 46 of the piston 44 is separated by a small gap G form the distal end 13 of the piston rod 12.

In a proceeding step 102 the lid 30 is closed thereby urging the cartridge 40 proximal direction 2 to pressurize or to axially squeeze at least one of the interior 45 of the cartridge 40 and the piston 44. In step 102 a distally facing support face 48, 49 of the cartridge 40 is brought in axial abutment with a distal support 50, 60 of the device 10 such that a proximal face 46 of the piston 44 gets pressurized by the distal end 13 of the piston rod 12, while the piston rod 12 is and remains in its proximal end position P.

LIST OF REFERENCE NUMBERS 1 distal direction
2 proximal direction
10 drug delivery device
11 drive mechanism
12 piston rod
13 distal end
14 pressure piece
15 distal face
16 gear
17 drive
18 battery
19 control
20 housing
21 interior
22 access opening
23 threaded support
30 lid
31 hinge
32 tube
33 connector
34 cannula
35 flap
36 inside face
37 closure
38 through opening
40 cartridge
41 distal end
42 proximal end
43 barrel
44 piston
45 interior
46 proximal face
47 distal seal
48 support face
49 support face
50 distal support
54 neck portion
55 head
56 shoulder portion
60 distal support
61 support member

The invention claimed is:

1. A drug delivery device for dispensing of a liquid medicament, the drug delivery device comprising:
a housing configured to accommodate a cartridge, the cartridge being filled with the medicament and having a piston slidably displaced within the cartridge along an axial direction and sealing a proximal end of the cartridge;
a drive mechanism comprising a piston rod extending along the axial direction and being at least displaceable in a distal direction from a proximal end position to displace the piston in the distal direction, wherein when the drive mechanism is in an initial configuration prior to dispensing or setting of an initial dose of the medicament, the piston rod is in the proximal end position; and
at least one distal support facing in a proximal direction to axially abut a distally facing support face of the cartridge;
wherein an axial distance between the at least one distal support and a distal end of the piston rod when the piston rod is in the proximal end position is smaller than an effective length of the cartridge, wherein the effective length of the cartridge is determined as the axial distance between a proximal face of the piston and the distally facing support face.

2. The drug delivery device according to claim 1, wherein the at least one distal support is located inside the housing and is configured to axially abut with a distally facing radially extending shoulder portion of the cartridge.

3. The drug delivery device according to claim 2, further comprising a support member immovably affixed to the housing thereby forming the at least one distal support.

4. The drug delivery device according to claim 2, further comprising a support member axially displaceable between a release position and a pre-tensed position.

5. The drug delivery device according to claim 1, wherein the housing comprises a lid movable between a release position and a locking position to selectively close an access opening of the housing through which the cartridge is insertable into an interior of the housing.

6. The drug delivery device according to claim 5, wherein an inside face of the lid forms the at least one distal support when the lid is in the locking position.

7. The drug delivery device according to claim 5, wherein the lid is pivotably attached to the housing.

8. The drug delivery device according to claim 5, wherein the lid comprises a through opening configured to receive a connector, the connector being configured to engage with a distal end of the cartridge in a fluid transferring way.

9. The drug delivery device according to claim 5, wherein the lid is configured to displace the cartridge in the proximal direction against the piston rod when pivoted from the release position into the locking position.

10. The drug delivery device according to claim 1, wherein the cartridge is arranged inside the housing.

11. The drug delivery device according to claim 10, wherein the distal end of the piston rod is in axial abutment with the proximal face of the piston of the cartridge when the cartridge is in axial abutment with the at least one distal support.

12. The drug delivery device according to claim 10, wherein at least one of an interior of the cartridge or the piston is pressurized or axially squeezed when the cartridge is axially supported by the at least one distal support while the piston rod is in the proximal end position.

13. The drug delivery device according to claim 1, wherein the drive mechanism further comprises an electric drive and a gear and wherein the piston rod is operably engaged with the electric drive via the gear.

14. The drug delivery device according to claim 13, wherein the gear is of a self-locking type.

15. A method of deploying a cartridge in a drug delivery device, the method comprising:
inserting the cartridge into a housing of the drug delivery device, wherein the cartridge is filled with a medicament and has a piston slidably displaced within the cartridge along an axial direction, wherein the piston seals a proximal end of the cartridge, and wherein the drug delivery device comprises:

a drive mechanism comprising a piston rod extending along the axial direction and being at least displaceable in a distal direction from a proximal end position to displace the piston in the distal direction, wherein when the drive mechanism is in an initial configuration and prior to dispensing or setting of an initial dose of the medicament, the piston rod is in the proximal end position; and at least one distal support facing in a proximal direction to axially abut a distally facing support face of the cartridge;

wherein an axial distance between the at least one distal support and a distal end of the piston rod when the piston rod is in the proximal end position is smaller than an effective length of the cartridge, wherein the effective length of the cartridge is determined as the axial distance between a proximal face of the piston and the distally facing support face; and pressurizing at least one of an interior of the cartridge or the piston by bringing the distally facing support face of the cartridge into axial abutment with the at least one distal support such that the proximal face of the piston is in abutment with the distal end of the piston rod, while the piston rod is in its proximal end position.

16. The method according to claim 15, wherein the at least one of the interior of the cartridge or the piston thereof is pressurized by moving a lid of the housing into a locking position thereby bringing an inside face of the lid in axial abutment with the distally facing support face of the cartridge prior to reaching the locking position, and displacing the cartridge in the proximal direction in the course of a further movement of the lid until the lid reaches the locking position.

17. A drug delivery device for dispensing of a liquid medicament, the drug delivery device comprising:
a housing configured to accommodate a cartridge, the cartridge being filled with the medicament and having a piston slidably displaced within the cartridge along an axial direction and sealing a proximal end of the cartridge;

a drive mechanism comprising a piston rod extending along the axial direction and being at least displaceable in a distal direction from a proximal end position to displace the piston in the distal direction; and at least one distal support facing in a proximal direction to axially abut a distally facing support face of the cartridge;

wherein an axial distance between the at least one distal support and a distal end of the piston rod when the piston rod is in the proximal end position is smaller than an effective length of the cartridge, wherein the effective length of the cartridge is determined as the axial distance between a proximal face of the piston and the distally facing support face;

wherein the at least one distal support is provided by a support member, wherein the at least one distal support is located inside the housing and is configured to axially abut with a distally facing radially extending shoulder portion of the cartridge;

wherein the support member is axially displaceable between a release position and a pre-tensed position.

* * * * *